United States Patent [19]

Evans

[11] Patent Number: 4,670,915

[45] Date of Patent: Jun. 9, 1987

[54] INTERCHANGEABLE EYESHIELD

[76] Inventor: Bradley J. Evans, P.O. Box 70112, Eugene, Oreg. 97401

[21] Appl. No.: 840,156

[22] Filed: Mar. 17, 1986

[51] Int. Cl.⁴ .............................................. A61F 9/02
[52] U.S. Cl. ......................................... 2/450; 2/443; 2/448; 351/116; 351/118
[58] Field of Search ................... 2/443, 446, 454, 448, 2/450, 439; 351/116, 118, 153, 110

[56] References Cited

U.S. PATENT DOCUMENTS

| | | | |
|---|---|---|---|
| 1,963,297 | 6/1934 | Eglinton | 351/110 |
| 2,513,507 | 7/1950 | Moeller | 351/116 X |
| 2,975,426 | 3/1961 | Rabb | 2/454 X |
| 3,233,249 | 2/1966 | Baratelli et al. | 2/443 |
| 3,394,980 | 7/1968 | Dym | 351/116 X |
| 3,574,452 | 4/1971 | McLendon | 351/116 X |
| 3,667,834 | 6/1972 | Davison et al. | 351/118 |
| 3,713,732 | 1/1973 | Gooch | 351/116 X |
| 3,744,887 | 7/1973 | Dunbar | 351/153 |
| 4,029,403 | 6/1977 | Harris | 351/116 X |
| 4,153,347 | 5/1979 | Myer | 351/116 X |
| 4,264,987 | 5/1981 | Runckel | 2/428 |

FOREIGN PATENT DOCUMENTS 3416912 11/1985 Fed. Rep. of Germany ...... 351/116

Primary Examiner—Peter Nerbun
Attorney, Agent, or Firm—Klarquist, Sparkman, Campbell, Leigh & Whinston

[57] ABSTRACT

An interchangeable eyeshield system comprises a plurality of interchangeable, frameless lenses and a pair of bows releasably engaged to a selected lens. Each lens is of a different color matched to a corresponding weather condition. The bows are each engaged to the lens selected for wear by a clasp hingedly attached to the temple portion of each bow and an aperture within the lens to receive the clasp. The length of the bow is adjustable to accommodate the head size of the wearer.

5 Claims, 7 Drawing Figures

U.S. Patent    Jun. 9, 1987    4,670,915
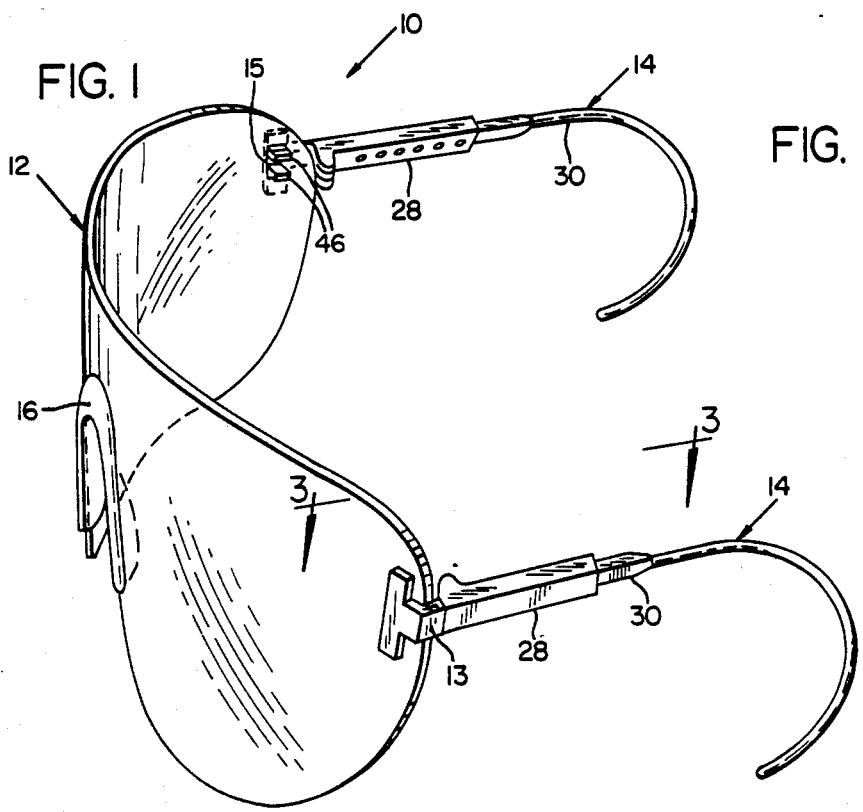
FIG. 1
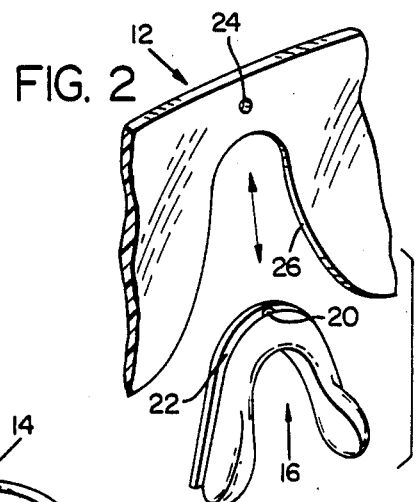
FIG. 2
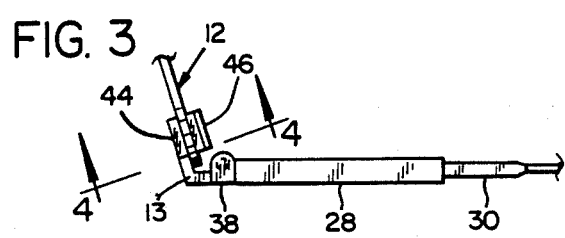
FIG. 3
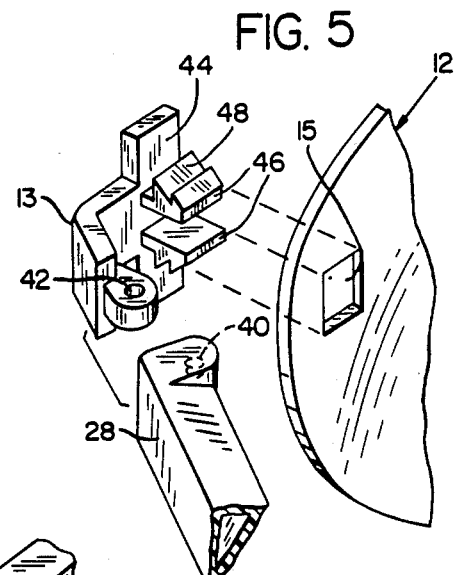
FIG. 5
FIG. 4
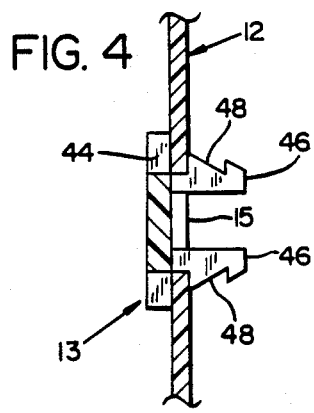
FIG. 6
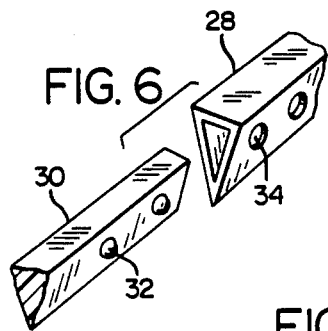
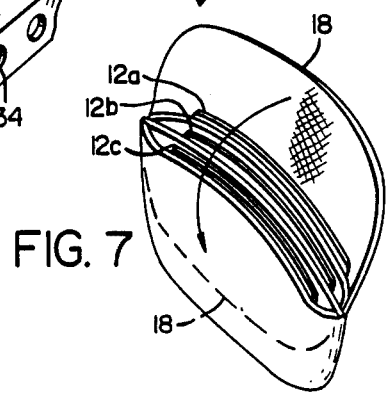
FIG. 7

4,670,915

INTERCHANGEABLE EYESHIELD

BACKGROUND OF THE INVENTION

This invention relates to eyeglasses and more particularly to an eyeshield having a plurality of interchangeable lenses.

Skiers, cyclists, joggers and other outdoor enthusiasts often wear protective glasses in a variety of weather conditions to shield their eyes from the elements. Different conditions, such as rain overcast, sun, and wind, call for different colors of lenses to maximize the wearer's perception. Typically, an amber lens is worn for overcast or foggy conditions, green or grey for sunny conditions, and magenta for partially sunny conditions.

Owning and carrying multiple pairs of eyeglasses for variable conditions, however, is cumbersome and expensive. Recognizing this, several types of eyeglasses are available that allow for interchangeability of the lenses to match the present weather condition, but each has drawbacks that limits it to a specific activity. Ski goggles, for example, are available with interchangeable lenses. But goggles are unwieldly, heavy and the frame blocks the peripheral vision necessary in other sports. Other eyeglasses offering interchangeability such as disclosed in U.S. Pat. No. 4,153,347 to Myer and U.S. Pat. No. 3,713,732 to Grooch suffer from this same drawback. Myer discloses interchangeable framed lenses that removably connect to bows. The frame is rigid and not easily flexed for storage. Grooch shows a two-part construction with a front frame connecting to a brow bar with attached bows. The Grooch design also is rigid and not easily stored. Both frames, moreover, do not shield adequately against wind or rain which can circumvent the frame edges.

An eyeshield with interchangeable lenses is disclosed in U.S. Pat. No. 2,513,507 to Moeller. The temple connection employed, though, relies on clamping action to hold the lens to the sidepieces. Such a connector is prone to slippage as the eyeshield is subjected to the shaking and pounding that occurs in strenuous activity.

Other attempts at developing eye wear with interchangeable lenses are disclosed in U.S. Pat. No. 3,744,887 to Dunbar and U.S. Pat. No. 3,574,452 to McLendon. In both these devices, however, the removable bows tend to separate from the frames under stress.

SUMMARY OF THE INVENTION

Accordingly, an object of the present invention is to provide a lightweight eyeshield in which the lenses can be freely interchanged, yet are securely attached to the bows when in place.

Another object of the invention is to provide such an eyeshield that does not impair peripheral vision.

Yet another object of the invention is to provide an eyeshield in which a group of interchangeable lenses can be conveniently carried by the wearer.

A further object of the invention is to provide an eyeshield that shields the eyes peripherally as well as forwardly.

To achieve these objects, an all-weather eyeshield system comprises a plurality of interchangeable, frameless lenses, a pair of bows for holding a lens selected to be worn for a specific weather condition, and a means for releasably engaging each bow to the selected lens. These means may comprise a male portion such as a clasp attached to each bow and a corresponding female portion such as an aperture within the lens to receive the male portion. With such a means and a number of lenses, the lens may be changed quickly and easily to match the present weather condition. In a narrower aspect of the invention, the clasp has a base portion and a pair of barbed, resilient projections extending outwardly from the base. The projections are squeezed together for inserting them through the aperture. Once through, the projections spread apart to fix the clasp securely to the lens.

The lens itself is preferably continuous and curved beyond the range of peripheral vision of the wearer. This design does not impair the view to the wearer and also shields thoroughly the eyes from dust and wind. The lens may include a removable nosepiece which is attached to the lens selected for wear. Each bow may also be longitudinally extensible to accommodate the size of the wearer.

The foregoing and other objects, features, and advantages of the invention will become more apparent from the following detailed description of a preferred embodiment which proceeds with reference to the accompanying drawings.

BRIEF DESCRIPTION OF THE DRAWINGS

FIG. 1 is a perspective view of an eyeshield according to the invention.

FIG. 2 is a partial view of the eyeshield sharing a removable nosepiece.

FIG. 3 is a plan view of FIG. 1 taken along line 3—3.

FIG. 4 is a cross-sectional view of FIG. 3 taken along line 4—4.

FIG. 5 is an exploded view of a clasp connecting each bow to the lens.

FIG. 6 is an exploded view of a bow.

FIG. 7 is a perspective view of the interchangeable lenses carried in a pouch.

DETAILED DESCRIPTION

Referring to FIG. 1, an all-weather eyeshield 10 according to the invention is shown. It comprises an interchangeable, frameless lens 12 and a pair of bows 14 releasably engaged to the lens for holding it to the face of the wearer. The connecting means for so engaging each bow 14 to lens 12 comprise male and female connectors, such as a clasp 13 and a corresponding aperture 15 within the lens to secure the clasp. The clasp 13 is also attached to each bow 14. These connecting means enable the wearer to select the lens 12 of a color matched to the present specific weather condition and install it easily in eyeshield 10. Also attached removably to the lens 12 selected by the wearer is a nosepiece 16, which can be custom fitted to the wearer's nose and switched between different lenses, as shown in FIG. 2. Alternatively, the nosepiece 16 may be integral with each lens 12.

The lens 12 is one of a plurality of flexible lenses each of a different color selected to be worn for a specific weather condition. Preferably at least three colored lenses are available—amber for minimal light conditions of fog and overcast, magenta for medium light conditions of partly sunny days, and gray for bright conditions such as reflection from snow, water, etc. Combinations of colors are also possible. Each lens comprises a continuous, flexible piece of material such as polycarbonate thermoplastic. In shape, lens 12 is continuously curved to wrap around the face of the wearer beyond the boundary of his peripheral vision to shield the eyes from the elements. The lenses 12a, 12b, 12c that are not being worn are conveniently stored in a portable closable pouch 18 shown in FIG. 7.

The nosepiece 16 may be removably attached to the lens 12 that is selected for wear. With this feature, the lens 12 may be interchanged while the wearer uses the same nosepiece. Preferably, the nosepiece is lined with a resilient material that adapts to fit properly to the bridge of the nose. As shown in FIG. 2, the nosepiece 16 includes a pin 20 at its apex and groove 22 within its outer edge. Lens 12 has a mating aperture 24 to receive the pin 20 and a ridge 26 that mates with the groove 22. The nosepiece 16 is removed by bending it sufficiently to withdraw the pin 20 from the aperture 24.

The bows 14 which are releasably engaged to the lens 12 are extensible, comprising a temple portion 28 and an ear portion 30 that are adjustably connected together to vary the length of the bow. FIG. 6 shows the structure of the bow 14 in detail. Ear portion 30 is longitudinal in part with a triangular cross section and plurality of protuberances 32 thereon. Temple portion 28 is hollow with similar cross section for slidably receiving the ear portion 30 and with a plurality of holes 34 for engaging the protuberances 32. The protuberances 32 and holes 34 clasp together to frictionally connect the temple and ear portions 28, 30. This adjustable connection enables the eyeshield 10 to accommodate the head size of the wearer.

The clasp 13 and aperture 15 for releasably engaging a bow 14 to one of the interchangeable lenses 12 are shown in detail in FIGS. 3 through 5. The clasp 13 is hingedly attached to the temple portion 28 at a hinge 38, which comprises pins 40 on temple portion 28 engaging a cylindrical housing 42 on the clasp 13. The pins 40 may be removed from housing 42 to replace either the clasp 13 or bow 14, if desired. The clasp 13 itself comprises a base portion 44 and a pair of barbed, resilient projections 46 extending outwardly from the base. The projections 46 squeeze together for insertion through the aperture 15, which is sized to receive them. Once through the aperture 15, the projections 46 spread apart, with the barbs 48 and the base 44 snugly engaging the lens 12 to fix the clasp 13 securely thereto. The clasp 13 is removed by squeezing the projections 46 together and withdrawing them through the aperture 15.

In wear, the lens 12 appropriate to the present weather condition is attached to the bow 12 and the other lenses are conveniently carried in pouch 18. If weather conditions change, the attached lens 12 can be quickly removed from the bows 14 and replaced by a lens of an appropriate color. The nosepiece 16 may also be interchanged if desired.

Having illustrated and described the principles of the invention in a preferred embodiment, it should be apparent to those skilled in the art that the invention can be modified in arrangement and detail without departing from such principles.

I claim all modifications coming within the spirit and scope of the following claims:

1. An eyeshield system for shielding the eyes of a wearer, comprising:
    a plurality of interchangeable, frameless continuous lenses each of a color selected to be worn for a specific weather condition, each lens having a pair of apertures therein;
    a pair of bows for supporting the selected lens, each bow comprising a temple portion and an ear portion adjustably connected together to vary the length of the bow; and
    a clasp pivotally hinged to each bow for removably engaging each bow to the selected lens and sized to engage the corresponding aperture in the selected lens to enable the lens to be supported without a frame, the clasp having a base portin and a pair of resilient projections extending outwardly from the base, each projection having a barb formed therein, and each base portion having at least one elongate lens engaging member extending outwardly therefrom further than the width of the barb, said lens engaging member being laterally spaced from each barb a distance equal to the thickness of said lens so as to permit said lens to be securely engaged therebetween;
    said projections being squeezed together for insertion through the aperture, after which said projections move apart for affixing the clasp securely to the lens, the lens being engaged between each barb and lens engaging member so as to prevent the movement of said lens during use.

2. The eyeshield of claim 1 including a nosepiece removably attached to the interchangeable lens selected for wear.

3. The eyeshield of claim 1 in which the ear portion is longitudinal in part with a plurality of protuberances thereon and the temple portion is hollow for slidably receiving the ear portion, the temple portion having a plurality of holes for engaging the protuberances of the ear portion to frictionally connect the temple and bow portions together.

4. The eyeshield of claim 1 in which each lens is continuously curved beyond the range of peripheral vision when supported by the bows.

5. The eyeshield system of claim 1 including a portable pouch for carrying the interchangeable lenses.

* * * * *